(12) United States Patent
Matov et al.

(10) Patent No.: US 7,746,339 B2
(45) Date of Patent: Jun. 29, 2010

(54) SYSTEM AND METHOD FOR AUTOMATIC DETECTION OF DENTAL FEATURES

(75) Inventors: Vadim Matov, San Jose, CA (US); Fuming Wu, Pleasanton, CA (US)

(73) Assignee: Align Technology, Inc., Santa Clara, CA (US)

( * ) Notice: Subject to any disclaimer, the term of this patent is extended or adjusted under 35 U.S.C. 154(b) by 856 days.

(21) Appl. No.: 11/457,722

(22) Filed: Jul. 14, 2006

(65) Prior Publication Data

US 2008/0014558 A1    Jan. 17, 2008

(51) Int. Cl.
*G06T 15/00*    (2006.01)
*A61C 3/00*    (2006.01)
*A61C 11/00*    (2006.01)
*A61C 9/00*    (2006.01)

(52) U.S. Cl. .................. 345/419; 433/24; 433/213; 433/214

(58) Field of Classification Search ............... 345/419; 433/24, 213–214
See application file for complete search history.

(56) References Cited

U.S. PATENT DOCUMENTS

| 5,605,459 | A | 2/1997 | Kuroda et al. | |
| 5,975,893 | A | 11/1999 | Chishti et al. | |
| 6,409,504 | B1 | 6/2002 | Jones et al. | |
| 6,441,816 | B1 * | 8/2002 | Nguyen et al. | 345/420 |
| 6,471,511 | B1 | 10/2002 | Chisti et al. | |
| 6,514,074 | B1 | 2/2003 | Chishti et al. | |
| 6,621,491 | B1 * | 9/2003 | Baumrind et al. | 345/419 |
| 6,685,469 | B2 | 2/2004 | Chishti et al. | |
| 6,767,208 | B2 | 7/2004 | Kaza | |
| 6,947,038 | B1 * | 9/2005 | Anh et al. | 345/419 |
| 7,063,532 | B1 | 6/2006 | Jones et al. | |
| 7,111,783 | B2 * | 9/2006 | Xi et al. | 235/437 |
| 7,194,394 | B2 * | 3/2007 | Dorfman et al. | 703/3 |
| 7,354,268 | B2 * | 4/2008 | Raby et al. | 433/24 |
| 2004/0113911 | A1 * | 6/2004 | Collodi | 345/426 |
| 2005/0219242 | A1 * | 10/2005 | Anh et al. | 345/419 |
| 2006/0073436 | A1 * | 4/2006 | Raby et al. | 433/24 |
| 2006/0204078 | A1 * | 9/2006 | Orth et al. | 382/154 |

FOREIGN PATENT DOCUMENTS

| GB | 2275154 | 8/1994 |
| WO | WO 00/19935 | 4/2000 |

* cited by examiner

*Primary Examiner*—Chante Harrison
(74) *Attorney, Agent, or Firm*—Brooks, Cameron & Huebsch, PLLC

(57) ABSTRACT

Systems and methods for automatic detection of dental features, such as cusps, ridges, and grooves, are disclosed. In accordance with an exemplary embodiment, a computer-implemented system and method for automatic detection of dental features for an occlusal surface of a patient's tooth comprises receiving three dimensional data for the tooth's occlusal surface, projecting the three dimensional data into a two dimensional plane, forming a height map from the projected three dimensional data, and detecting a set of points from the height map.

20 Claims, 12 Drawing Sheets

Line of Occlusion

FIG. 11B

SYSTEM AND METHOD FOR AUTOMATIC DETECTION OF DENTAL FEATURES

FIELD OF INVENTION

The present invention relates generally to the field of orthodontics, and in particular to systems and methods for automatic detection of dental features.

BACKGROUND OF THE INVENTION

One objective of orthodontics is to move a patient's teeth to positions where the teeth function optimally and are also aesthetically pleasing. Conventional appliances such as braces and wires are applied to the teeth of a patient by an orthodontist. Once mounted on the teeth, the braces exert continual force on the teeth and gradually urge the teeth to their respective ideal position. The orthodontist does this by adjusting the braces over time to move the teeth toward their final destination.

Orthodontic brackets are often bonded directly to the patient's teeth. Typically, a small quantity of adhesive is placed on the base of each bracket and the bracket is then placed on a selected tooth. Before the adhesive is set, the bracket is maneuvered to a desired location on the tooth. Once the adhesive has hardened, the bracket is bonded to the tooth with sufficient strength to withstand subsequent orthodontic forces as treatment progresses. One shortcoming with this technique is the difficulty in accessing the optimal surface for bracket placement on severely crowded teeth or in teeth where the bonding surface is obstructed by teeth in the opposing arch during jaw closure. With posterior teeth, the treatment provider may have difficulty seeing the precise position of the bracket relative to the tooth surface. The amount of time needed to carry out the bonding procedure may be a nuisance both to the patient as well as to the treatment provider. Also, the necessity of minimizing moisture contamination from the patient's saliva can prolong the procedure and also unduly impair the accuracy of placement of the brackets on the teeth. All of these factors increase the chance that one or more brackets will be incorrectly positioned on the teeth.

Apparatus, systems, and methods have been developed to facilitate teeth movement utilizing clear, removable teeth aligners as an alternative to braces. A mold of the patient's bite is initially taken and desired ending positions for the patient's teeth (i.e., a functionally and aesthetically optimum position) are determined, based on a prescription provided by an orthodontist or dentist. Corrective paths between the initial positions of the teeth and their desired ending positions are then planned. These corrective paths generally include a plurality of intermediate positions between the initial and ending positions of the teeth. Multiple clear, removable aligners formed to move the teeth to the various positions along the corrective path are then manufactured. One system for providing such aligners is the Invisalign® System from Align Technologies, Inc. of Santa Clara, Calif.

Tooth anatomy features, such as cusps, ridges, and grooves, also need to be evaluated in order to determine the proper corrective paths and the teeth's desired ending positions.

The upper and lower jaws should fit well together and the occlusal curve for the upper and lower jaws should be well aligned and smooth. In order to evaluate the various characteristics of the occlusal curves of the upper and lower jaws, it is necessary to measure various dental features. Automatic detection of these dental features would save time and eliminate human error, thus improving the accuracy of the dental measurements.

SUMMARY OF THE INVENTION

Systems and methods for automatic detection of dental features, such as cusps, ridges, and grooves, are disclosed. In accordance with an exemplary embodiment, a computer-implemented system and method for automatic detection of dental features for an occlusal surface of a patient's tooth comprises receiving three dimensional data for the tooth's occlusal surface, projecting the three dimensional data into a two dimensional plane, forming a height map from the projected three dimensional data, and detecting a set of points from the height map.

BRIEF DESCRIPTION OF THE DRAWINGS

A more complete understanding of the present invention may be derived by referring to the detailed description and claims when considered in connection with the drawing Figures, where like reference numbers refer to similar elements throughout the Figures, and:

DETAILED DESCRIPTION OF THE INVENTION

The present invention may be described herein in terms of various components and processing steps. It should be appreciated that such components and steps may be realized by any number of hardware and software components configured to perform the specified functions. For example, the present invention may employ various electronic control devices, visual display devices, input terminals and the like, which may carry out a variety of functions under the control of one or more control systems, microprocessors or other control devices. In addition, the present invention may be practiced in any number of orthodontic contexts and the exemplary embodiments relating to a system and method for automatic detection of dental features are merely a few of the exemplary applications for the invention. For example, the principles, features and methods discussed may be applied to any orthodontic treatment application.

U.S. patent application Ser. Nos. 09/264,547 and 09/311,716, now U.S. Pat. No. 6,514,074 describe techniques for generating 3-dimensional digital data sets containing models of individual components of a patient's dentition. These data sets include digital models of individual teeth and the gingival tissue surrounding the teeth. Furthermore, these applications also describe computer-implemented techniques for using the digital models in designing and simulating an orthodontic treatment plan for the patient. For example, one such technique involves receiving an initial data set that represents the patient's teeth before treatment, specifying a desired arrangement of the patient's teeth after treatment, and calculating transformations that will move the teeth from the initial to the final positions over desired treatment paths. U.S. patent application Ser. No. 09/169,276 also describes the creation of data sets representing the tooth positions at various treatment stages and the use of these data sets to produce orthodontic appliances that implement the treatment plan. One technique for producing an orthodontic appliance involves creating a positive mold of the patient's dentition at one of the treatment stages and using a conventional pressure molding technique to form the appliance around the positive mold. A design of orthodontic appliances from the digital dentition models is, for example, described in U.S. patent application Ser. No. 09/169,034.

Figure 1A:
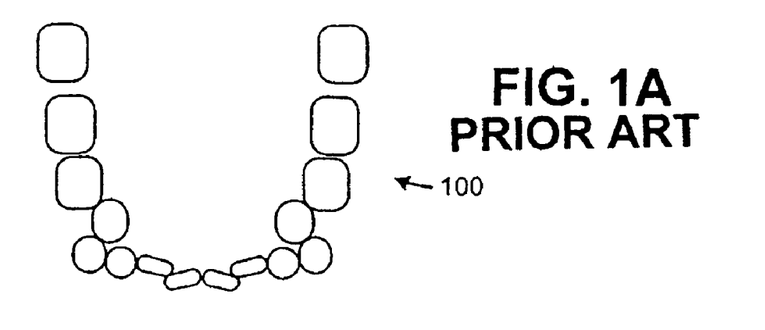
FIGS. 1A, 1B, and 1C are diagrams showing the arrangement of a patient's teeth at an initial stage, an intermediate stage, and a final stage, respectively, of orthodontic treatment.
Figure 1B:
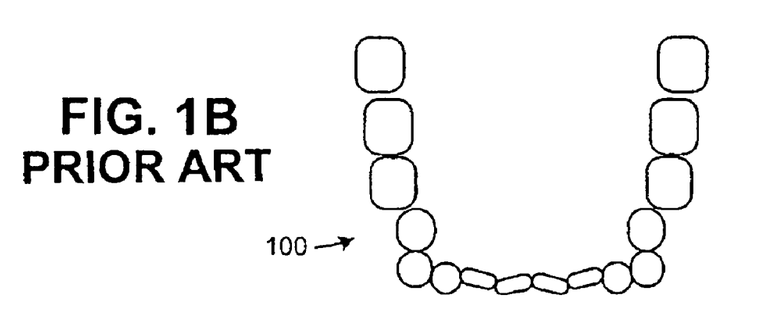
Figure 1C:
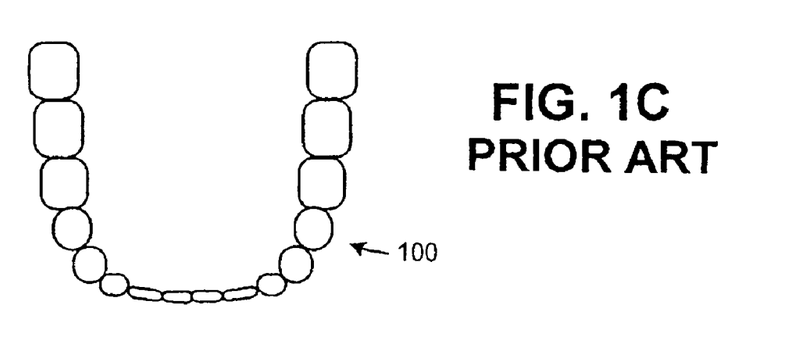

FIGS. 1A, 1B, and 1C show a patient's dentition at three stages during a course of treatment. FIG. 1A illustrates the initial positions of the patient's teeth before treatment begins. A digital model of the teeth at these initial positions is captured in an initial digital data set (IDDS).

Such an IDDS may be obtained in a variety of ways. For example, the patient's teeth may be scanned or imaged using well known technology, such as X-rays, three-dimensional x-rays, computer-aided tomographic images or data sets, magnetic resonance images, and the like.

Methods for digitizing such conventional images to produce data sets are well known and described in the patent and medical literature. By way of example, one approach is to first obtain a plaster cast of the patient's teeth by well known techniques, such as those described in Graber, Orthodontics: Principle and Practice, Second Edition, Saunders, Philadelphia, 1969, pp. 401-415. After the tooth casting is obtained, it can be digitally scanned using a conventional laser scanner or other range acquisition system to produce the IDDS. The data set produced by the range acquisition system may, of course, be converted to other formats to be compatible with the software which is used for manipulating images within the data set. General techniques for producing plaster casts of teeth and generating digital models using laser scanning techniques are described, for example, in U.S. Pat. No. 5,605,459. In accordance with another exemplary embodiment, the acquiring of a digital model of a patient's teeth can also comprise such techniques as disclosed in U.S. Pat. No. 6,767,208, entitled "System and Method for Positioning Teeth", assigned to Align Technology, Inc. Accordingly, any methodology or process for converting scanned data into a digital representation or otherwise for the acquiring of a digital model of a patient's teeth can be utilized.

FIG. 1B illustrates an example of how the patient's teeth may be oriented at an intermediate stage in the treatment process, and FIG. 1C illustrates an example of how the patient's teeth may be oriented at their final positions. A human operator and/or a computer program manipulate the digital models of the patient's teeth to prescribe the final tooth positions. The program then calculates one or more of the intermediate positions, taking into account any constraints imposed on the movement of the teeth by the human operator or by the natural characteristics of the teeth themselves. The program also accounts for any collisions that might occur between teeth as the teeth move from one treatment stage to the next. Selecting the final and intermediate tooth positions and the treatment paths along which the teeth move is described in more detail in one or more of the Patent Applications discussed above, which are all hereby incorporated by reference, in their respective entireties.

Figure 1D:
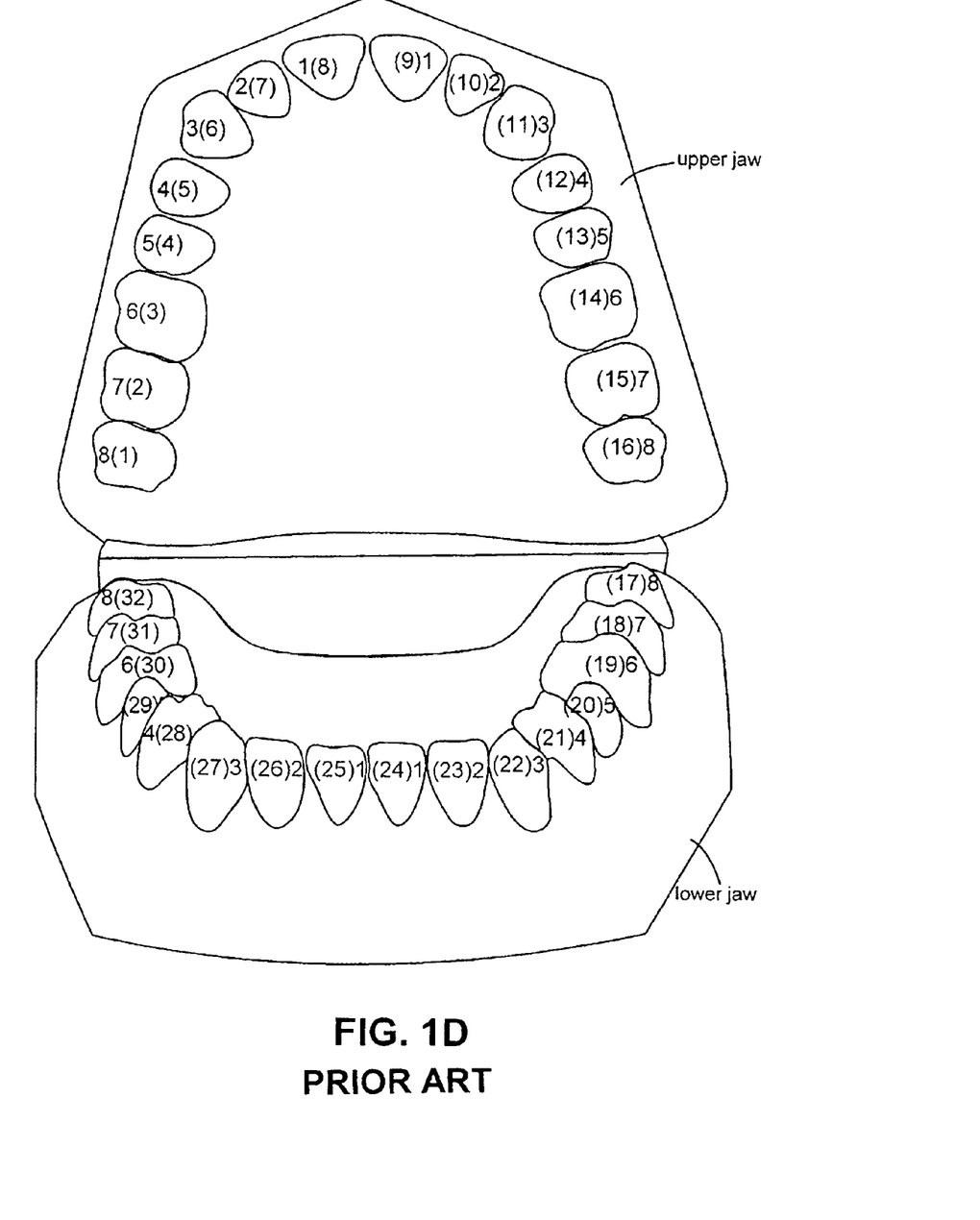
FIG. 1D is a diagram showing teeth numbering according to the standard system of tooth numbering.

FIG. 1D is a diagram of a set of teeth showing the standard system of numbering teeth. Reference is made to this standard system of numbering throughout the discussion below.

Figure 2:
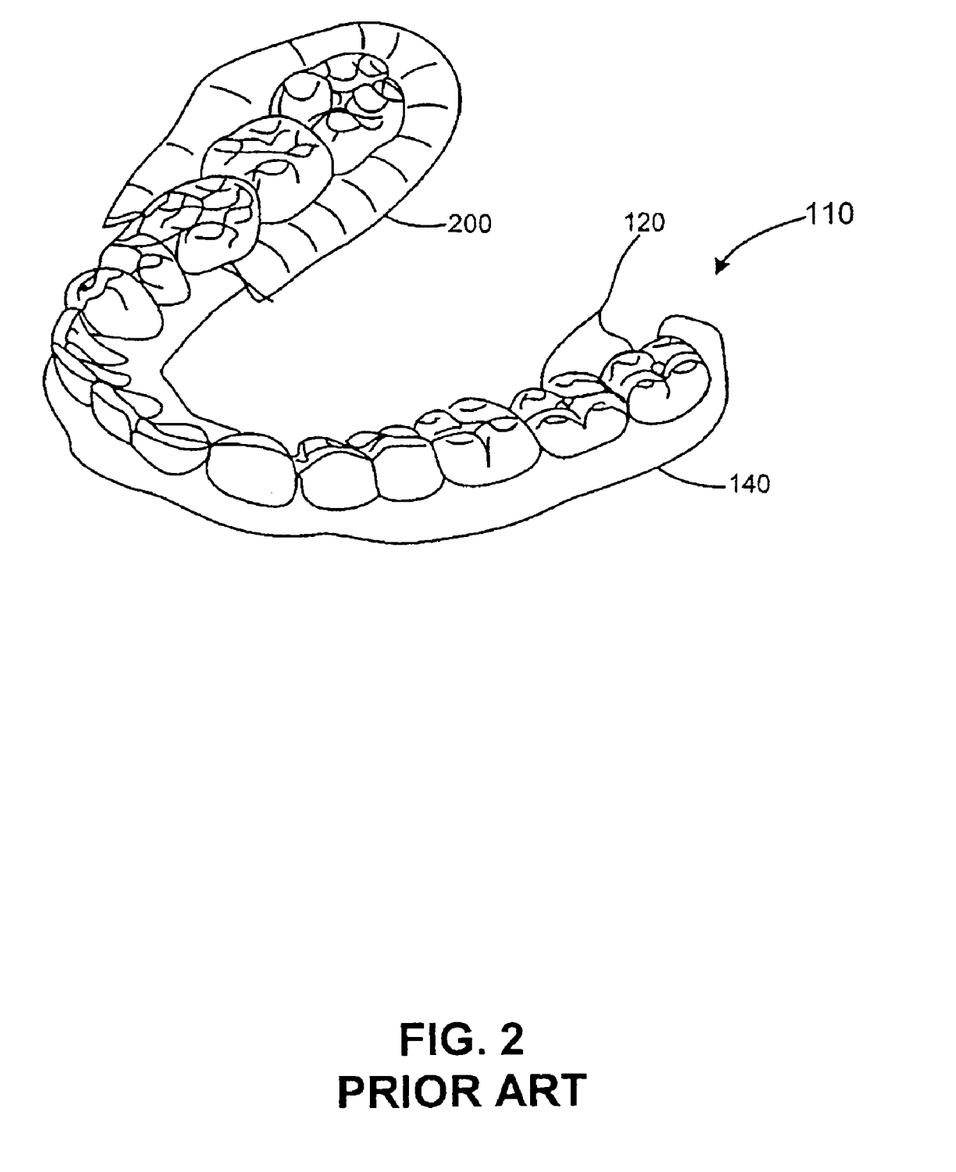
FIG. 2 is a diagram illustrating a partial model of a patient's dentition, including a model of gingival tissue.

FIG. 2 is a diagram illustrating a portion of a typical digital dentition model 110 derived from the IDDS. Dentition model 110 includes models of individual teeth 120 and a model of the patient's gums 140. Various techniques for creating models of gum tissue and individual teeth from the IDDS are described in, for example, U.S. patent application Ser. Nos. 09/264,547 and 09/311,941.

Furthermore, FIG. 2 shows a portion of another gingival model 200 (a "secondary" gingival model), which is constructed to overlie gingival model 140 derived from the IDDS (the "primary" gingival model). The program uses the secondary gingival model 200 to model the deformation of the gingival tissue around the patient's teeth as the teeth move from their initial positions to their final positions. This ensures that orthodontic appliances made from positive molds of the patient's dentition fit comfortably around the patient's gums at all treatment stages. The secondary gingival model 200 also adds thickness to the gum model, which ensures that the orthodontic appliances do not press too tightly against the patient's gums.

Reference will now be made to various exemplary embodiments of the invention, which are illustrated in the accompanying figures. While these exemplary embodiments are described in sufficient detail to enable those skilled in the art to practice the invention, it should be understood that other embodiments may be realized and that logical and/or mechanical changes may be made without departing from the spirit and scope of the invention. Thus, the various embodiments herein are presented for purposes of illustration and not by way of limitation. For example, the steps recited in any of the method or process descriptions may be executed in any order and are not limited to the order presented. Moreover, any of the functions or steps may be outsourced to or performed by one or more third parties.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical connections between the various elements. It should be noted that many alternative and/or additional functional relationships or physical connections may be present in a practical system.

Various embodiments of the present invention include one or more computing devices having programs stored therein for staging the movement of a patient's teeth. The computing device(s) or various components of any computing device discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various file indexes and/or databases used herein may include: client data; merchant data; and/or other similar useful data.

As those skilled in the art will appreciate, any computing device utilized by a user may include an operating system (e.g., Windows NT, 95/98/2000, OS2, UNIX, Linux, Solaris, MacOS, etc.) as well as various conventional support software and drivers typically associated with computers. As will be appreciated by one of ordinary skill in the art, each computing device may be embodied as a customization of an existing system, an add-on product, upgraded software, a stand alone system, a distributed system, a method, a data processing system, a device for data processing, and/or a computer program product. Accordingly, any program stored therein may take the form of an entirely software embodiment, an entirely hardware embodiment, or an embodiment combining aspects of both software and hardware. Furthermore, any program may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

In accordance with one exemplary embodiment, a computing device is configured to receive an electronic representation of the patient's teeth in an initial position taken by, for example, an intra-oral scanner or a CT scanner based on an impression or partial impression of the patient's teeth. The received data includes three dimensional data for the patient's teeth that can be used as input into the various embodiments of the present invention for automatic detection of the teeth's features. In addition, the computing device is configured to receive or generate an electronic representation of a desired final position for each of the patient's teeth. The program stored within the computing device is configured to analyze the initial and final positions, and automatically create a route for each tooth to move from its initial position to its final position. A set of aligners to move the teeth along the path in various stages is manufactured for the patient. As the patient wears the aligners, the patient's teeth move along the path according to each stage.

In order to analyze the initial and final positions of the teeth, analysis of the occlusal curve of the upper and lower jaw may be undertaken. In addition, an analysis of the fit or "bite" between the upper and lower jaw may also be undertaken, especially with respect to how the molars of the upper and lower jaw fit together. In order to assist this analysis, measurements utilizing the various features of the teeth are undertaken. In order to assist these measurements, the present invention provides for automatic detection of various features, such as cusps, ridges, and/or grooves, of the teeth.

Figure 3:
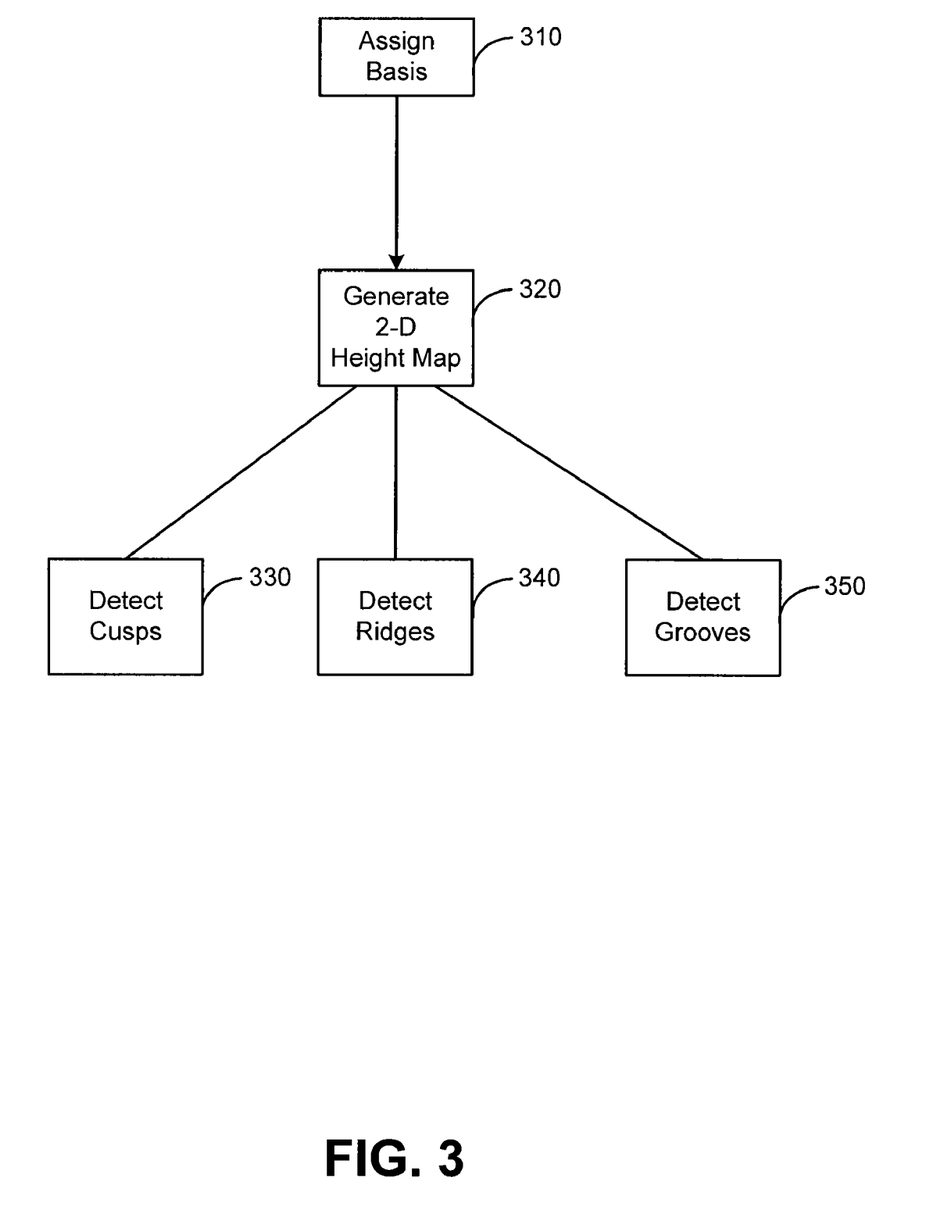
FIG. 3 is a flow diagram illustrating an exemplary process for automatic detection of dental features.

FIG. 3 is a flow diagram illustrating an exemplary process for automatic detection of dental features. First, each tooth is assigned with an orthogonal (i.e., x,y,z) frame of reference that is referred to as the basis (310). The received three dimensional data for the teeth is used to generate a two dimensional height map, for a tooth, by projecting the three dimensional data of the tooth's occlusal surface into two dimensions in the occlusal direction (i.e, direction of the z-axis) (320). Utilizing the 2-d height map, cusps (330), ridges (340), and/or grooves (340) can be automatically detected.

Figure 4:
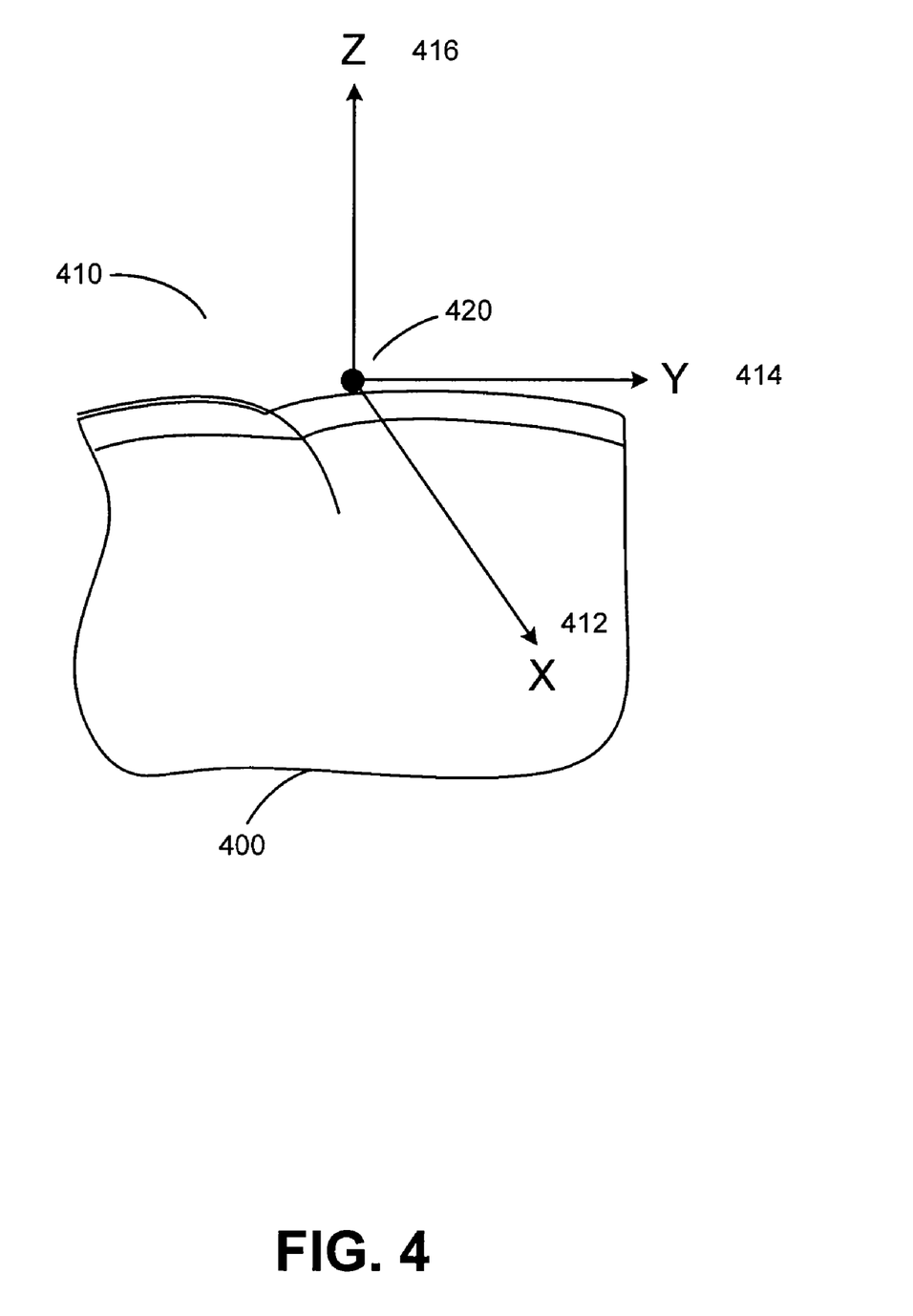
FIG. 4 illustrates an exemplary axis of reference for a patient's teeth.

With reference to FIG. 4, each tooth 400 may be assigned an orthogonal frame 410 of reference with an x-axis 412, y-axis 414, and z-axis 416. Orthogonal frame of reference 410 may also be referred to as a basis. In accordance with an embodiment of the present invention, x-axis 412 is aligned in the buccal-lingual direction, which is the direction between the cheek and tongue. Y-axis 414 is aligned in the mesial-distal direction, which is the direction between the front of the mouth and the back of the mouth. Z-axis 416 is aligned in the occlusal-root direction, which is the direction from the top of the tooth to the part of the tooth in the gum. It will be appreciated that in other embodiments of the present invention, the x-axis, y-axis, and z-axis, may be interchanged with each other. The intersection of the three axes is a point 420 that is proximate to the center of the clinical crown of the tooth.

Figure 6:
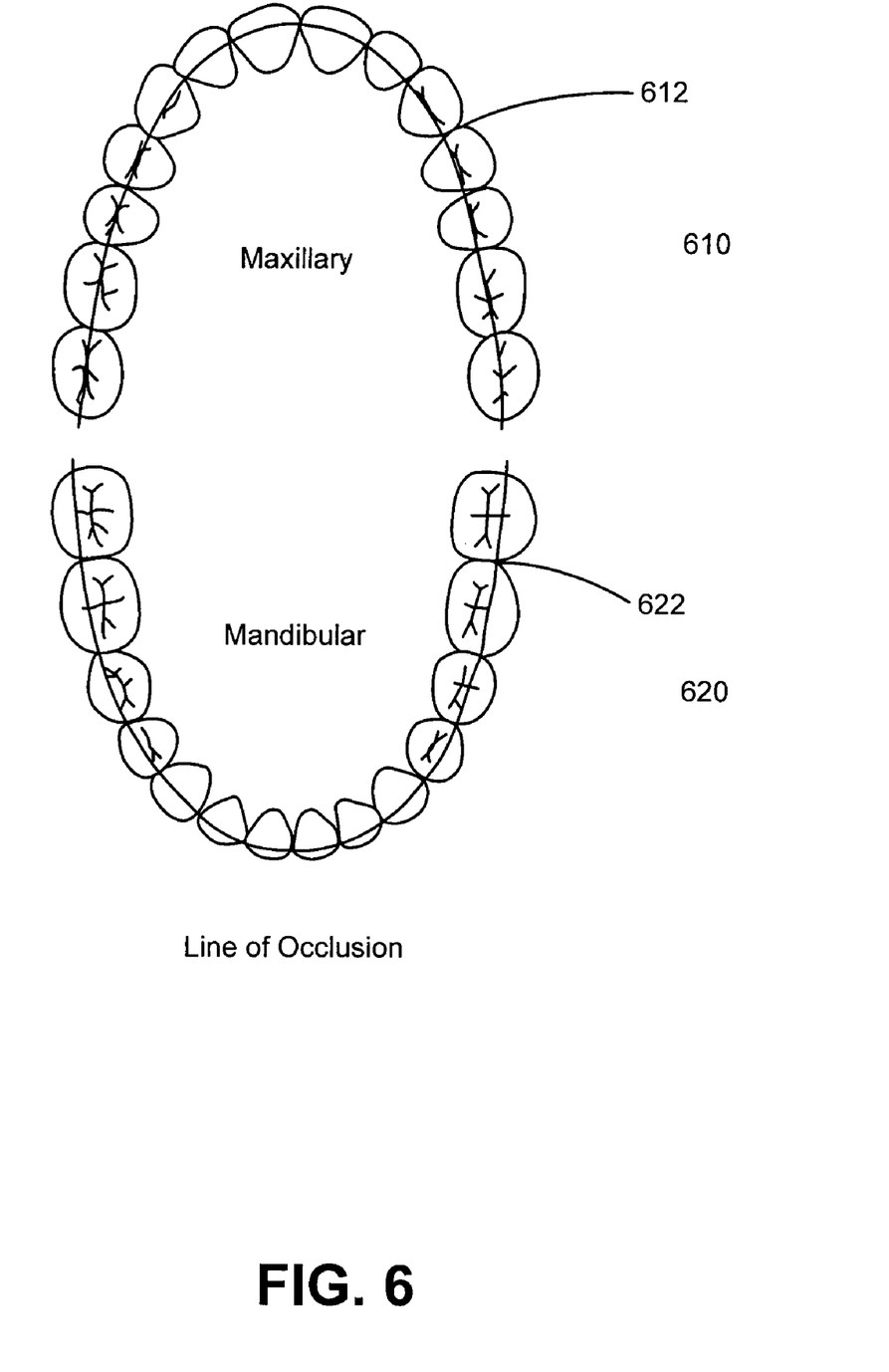
FIG. 6 is a diagram illustrating line of occlusion for an exemplary upper and lower jaw.
Figure 7:
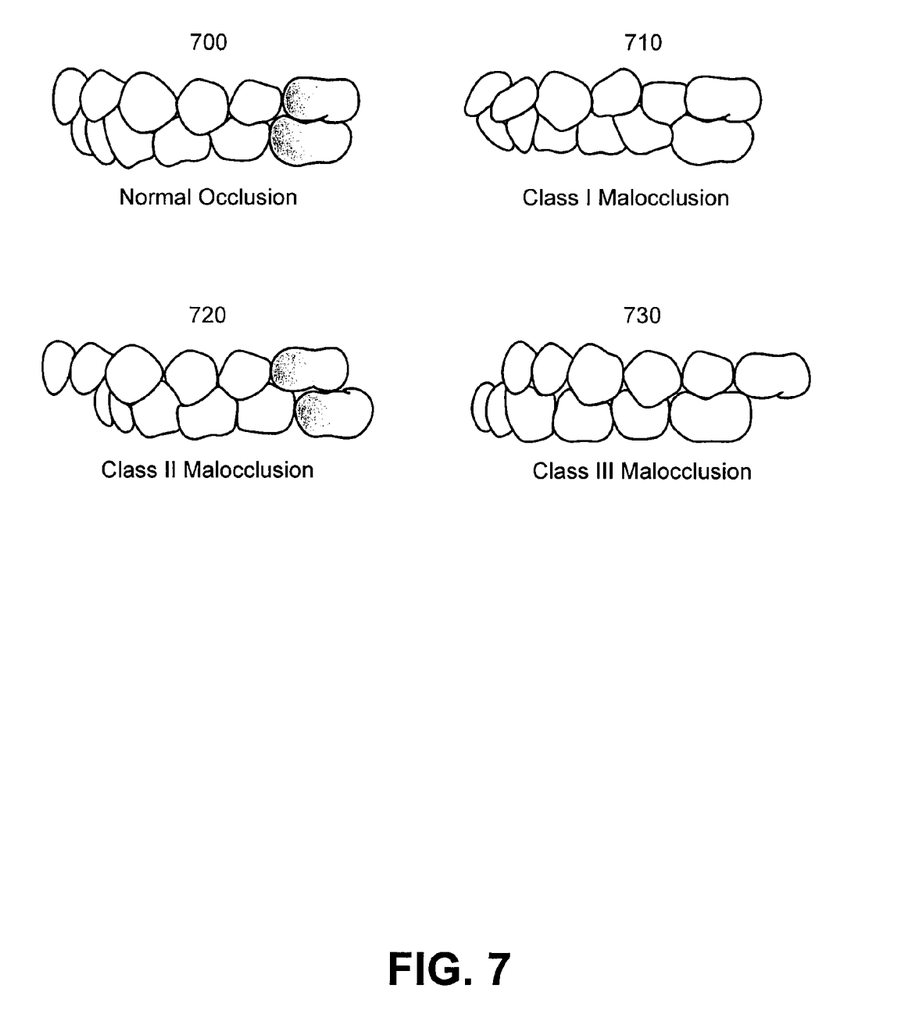
FIG. 7 is a diagram illustrating the various classes of normal occlusion and malocclusion.

Cusps are major tooth anatomy features that are important in determining the class of malocclusion. With reference to FIGS. 6 and 7, normal occlusion 700 occurs when the upper and lower molars fit together such that the mesiobuccal cusp of the upper molar occludes in the buccal groove of the lower molar. In addition, with reference to FIG. 6, for a case of normal occlusion, the teeth of the upper 610 and lower 620 jaws should be arranged in a smoothly curving line of occlusion 612, 622. Class I malocclusion 710 occurs when the relationship of the molars is normal, but the line of occlusion 612, 622 is incorrect because of misaligned teeth, rotations, or other causes (e.g., crowded teeth, crooked teeth, turned teeth). Class II malocclusion 720 occurs when the lower molar is distally positioned relative to the upper molar (i.e., overbite or "buck teeth"). Class III malocclusion 730 occurs when the lower molar is mesially positioned relative to the upper molar (i.e., underbite). Establishing the class of occlusion involves detection of the cusps such that the fit of the molars of the upper jaw to the molars of the lower jaw can be measured.

Figure 5:
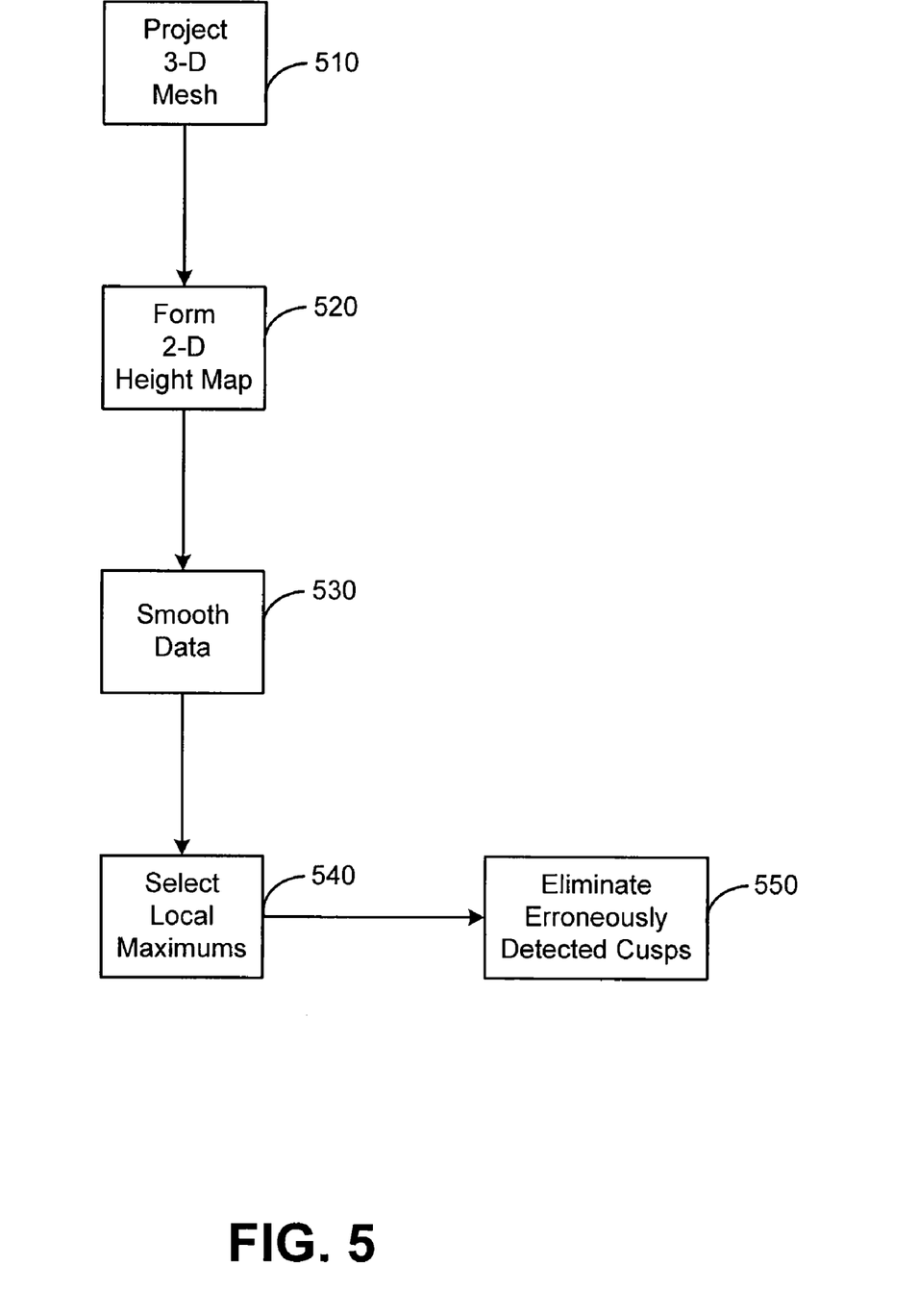
FIG. 5 is a flow diagram illustrating an exemplary process for automatic detection of cusps.
Figure 10A:
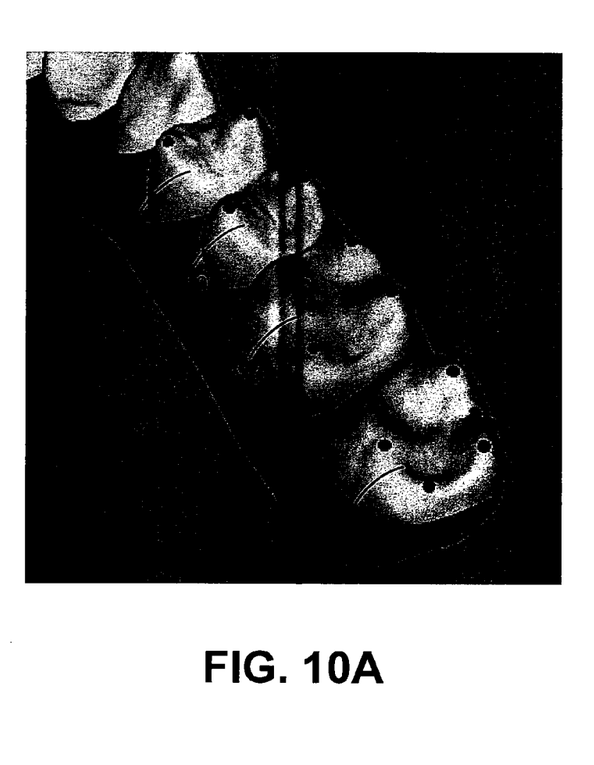
FIGS. 10A-B illustrate exemplary detected cusps in accordance with the exemplary process of FIG. 5.
Figure 10B:
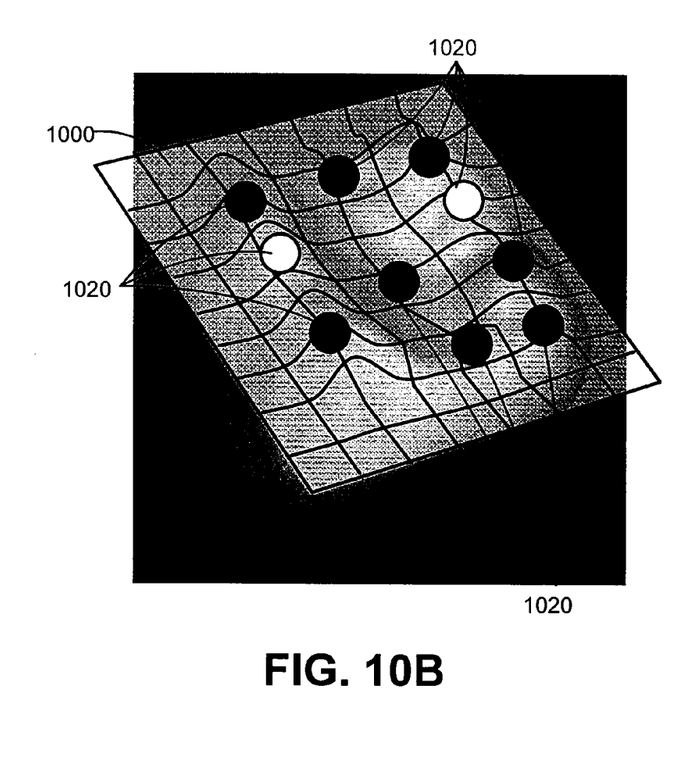

As mentioned above, input data is received in the form of three dimensional data that represents the initial position of the teeth. In accordance with one embodiment of the present invention, this input data is in the form of a three dimensional mesh model (i.e., a series of interconnected triangles) that is used to represent the teeth's surface. With reference to FIGS. 5 and 10A-B, in an exemplary embodiment, cusps may be automatically detected from a tooth's three dimensional mesh model 1000. First, for a given tooth, three dimensional mesh model 1000 of a tooth's occlusal surface 1010 is sampled and projected in the occlusal direction of the teeth (step 510). In this step, and in accordance with this exemplary embodiment of the present invention, each point from the three dimensional mesh for the tooth's occlusal surface is projected in the direction of z-axis 416 onto a two dimension plane. The resulting projected data is used to form a two dimensional height map of the tooth's occlusal surface (step 520). In accordance with this embodiment of the present invention, each point of the two dimensional height map corresponds to a vertex from the mesh for the tooth's occlusal surface. The "value" of each point of the height map corresponds to the relative height of the occlusal surface at a given vertex of the three dimensional mesh. Stated another way, a height map for the tooth's occlusal surface is built by sampling and projecting the three dimensional data from the tooth's occlusal surface into the direction of z-axis 416 of the tooth's frame of reference 410.

After the two dimensional height map is generated by sampling and projecting a mesh model of the three dimensional tooth in the occlusal direction, or z-axis 416 of the tooth's frame of reference 410, the two dimensional height map data is smoothed to reduce the noise in the data (step 530) by running the 2-d data through a smoothing filter. Detection of the local maxima points 1020 occurs by traversing the data in the resulting smoothed two dimensional height map and selecting the maximum values in a local area (step 540). In accordance with one embodiment of the present invention, a local area is an area of size that corresponds to the tooth's occlusal surface. The size of the local area may be configurable, for example, by use of a parameter to the computer program. This and other parameters may be read from a configuration file (e.g., parameter file) or may be entered by user in response to one or more prompts from the computer program. The detection of local maxima points 1020 may result in more points than the number of cusps for a given tooth (i.e., four cusps for molars, two cusps for pre-molars or bicuspids). This could be due to data noise, variations in the tooth shape, or other factors.

Erroneously detected cusps can be eliminated (step 550) using the following set of rules. If two maximum points 1020 are close in location, that is, within a pre-defined (i.e., configurable) fraction of the buccal-lingual width of the tooth, the lower point (i.e., smaller height value) is removed from the list of detected cusps. One rationale for this is that cusps typically are not found within close proximity of each other. Furthermore, cusps are typically located near tooth edges and away from the central groove of the tooth. Thus, if any of the detected maximum points are located in close proximity to the tooth's central groove, that is, within the pre-defined fraction of the buccal-lingual width of the teeth, then the detected point is eliminated from the list of detected cusps. Finally, only two maximum points are preserved on each of the buccal (i.e., cheek) and lingual (i.e., tongue) sides. Therefore, after erroneous cusps are removed, the total number of cusps for each molar should be less than or equal to four and the total number of cusps for each pre-molar should be less than or equal to two.

Figure 8:
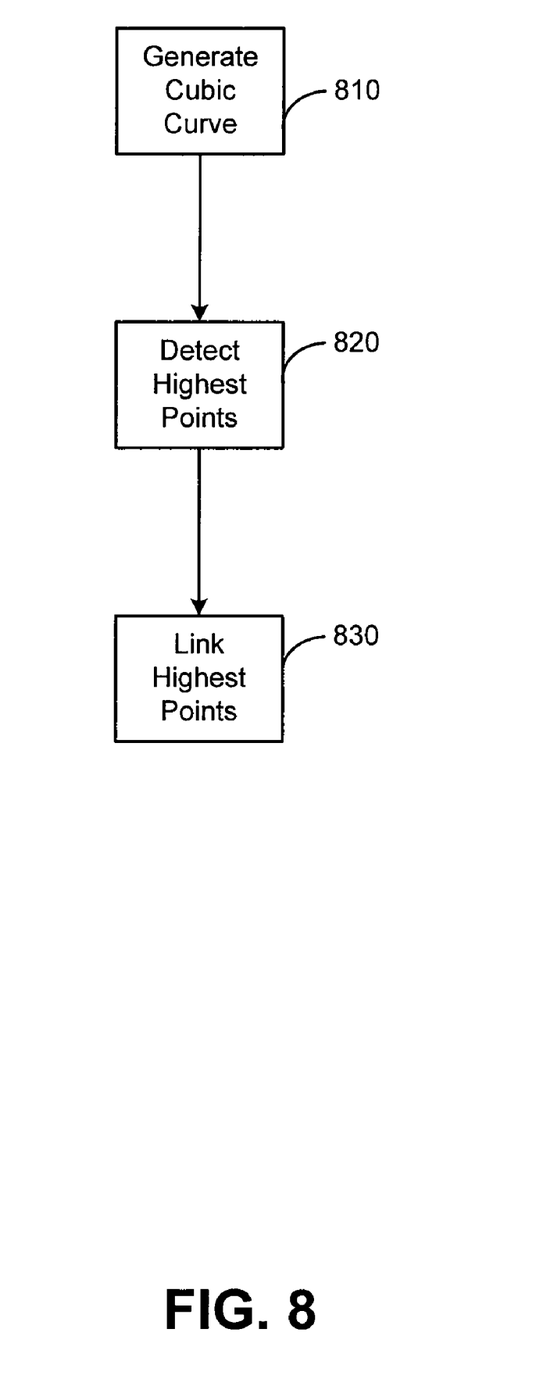
FIG. 8 illustrates flow diagram illustrating an exemplary process for automatic detection of ridges.
Figure 11A:
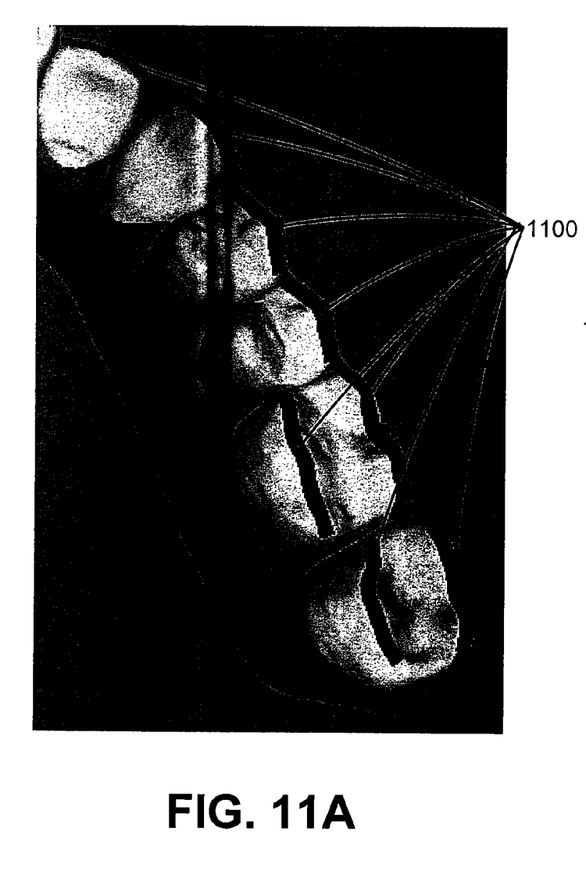
FIGS. 11A-B illustrate and exemplary detected ridge in accordance with the exemplary process of FIG. 8.
Figure 11B:
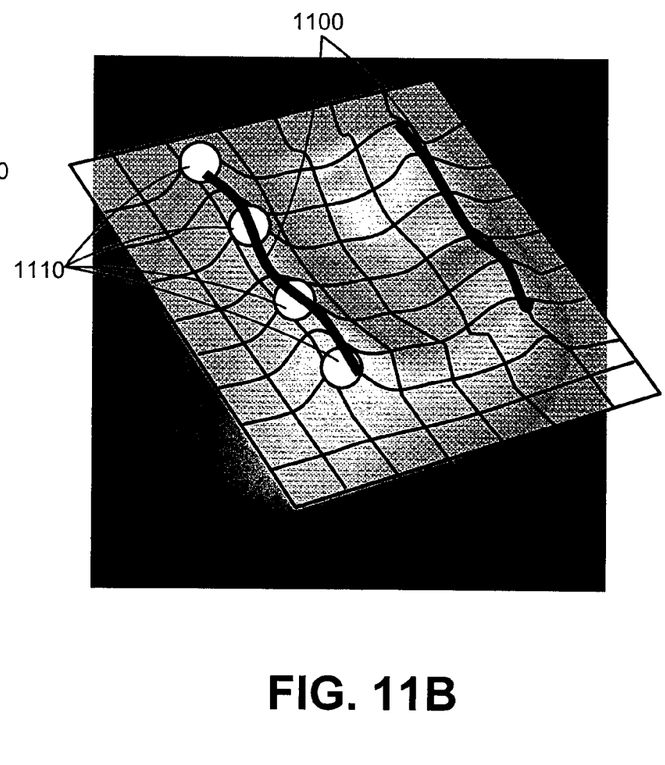

In accordance with an exemplary embodiment, with reference to FIGS. 8 and 11A-B, ridges for a tooth can be automatically detected using data from the two dimensional height map for the tooth's occlusal surface. For molars and premolars, buccal and lingual ridges may be automatically detected. For incisors and canines, occlusal ridges may be automatically detected.

After the two dimensional height map is generated as previously discussed, a set of cubic curves 1100 is generated in planes perpendicular to the direction of y-axis 414, using nearby data points (step 810) that are within a pre-defined (i.e., configurable, for example, by a program parameter) distance of each other. After the set of cubic curves 1100 is generated, the highest points 1110 in each cubic curve are detected (step 820) by examining the two dimensional height map data for the points of the curve. The detected highest points are then linked to form an edge curve that corresponds to a ridge (step 830) for the tooth. This technique is used to detect buccal (i.e., along the cheek) and lingual (i.e., along the tongue) ridges for molars and pre-molars, and occlusal (i.e., along the top surface of the tooth) ridges for incisors and canines.

Figure 9:
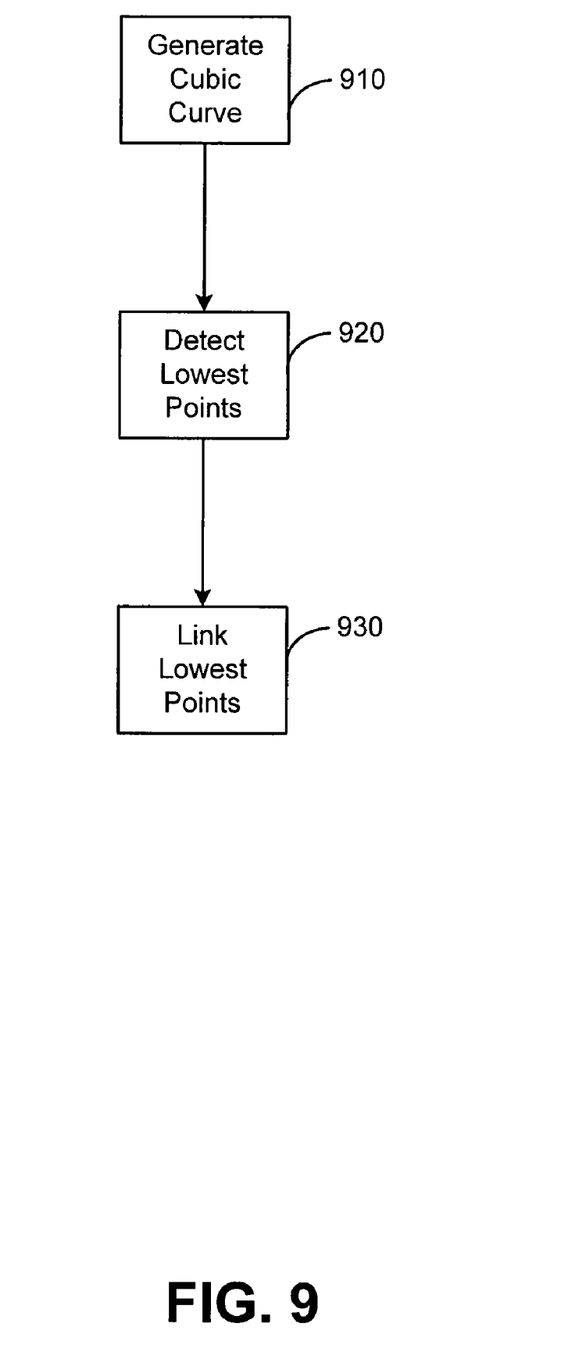
FIG. 9 flow diagram illustrating an exemplary process for automatic detection of grooves.

In accordance with an exemplary embodiment, with reference to FIG. 9, grooves can be automatically detected using data from the two dimension height map. As with ridge detection, a set of cubic curves is generated in planes perpendicular to the y-direction using the nearby data points (step 910). The lowest points in the cubic curve are detected (step 920) by examining the two dimensional height data for each point of the curve. The detected lowest points are then linked to form an edge curve that corresponds to a ridge (step 930) for the tooth. This technique can be used to detect the central grooves of molars and pre-molars.

Additional information on dental features and various techniques for determining the final position of teeth are described in U.S. Pat. No. 6,685,469.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims.

We claim:

1. A computer-implemented method for automatic detection of a plurality of cusps for an occlusal surface of a patient's tooth, comprising:
    a) receiving three dimensional data for the tooth's occlusal surface;
    b) projecting the three dimensional data into a two dimensional plane;
    c) forming a height map from the projected three dimensional data;
    d) detecting a plurality of local maximum points from the height map; and
    e) removing at least one erroneously detected local maximum point, wherein the erroneously detected local maximum point comprises:
        one of the plurality of local maximum points from the height map; and
        a lower point from a set of two of the plurality of maximum points, wherein the set of two maximum points are located within a pre-defined distance of each other;
    wherein the method is performed by a computer.

2. The computer-implemented method of claim 1, further comprising:
    smoothing the height map.

3. The computer-implemented method of claim 1, wherein the step of removing at least one erroneously detected local maximum point comprises:
    removing one of the plurality of detected local maximum point that is located within a pre-defined distance of a center groove of the tooth.

4. The computer-implemented method of claim 1, wherein the method further comprises:
    preserving two of the plurality of detected local maximum points on each of a buccal and a lingual side of the tooth, wherein the tooth is a molar.

5. A computer-implemented method for automatic detection of a ridge for an occlusal surface of a patient's tooth, comprising:
    a) receiving three dimensional data for the tooth's occlusal surface;
    b) projecting the three dimensional data into a two dimensional plane;
    c) forming a height map from the projected three dimensional data;
    d) forming a set of cubic curves in a first direction from the height map;

e) detecting a high point from the height map data for each of a plurality of cubic curves of the set of cubic curves; and f) linking the high points from the plurality of cubic curves of the set of cubic curves to form a curve in a second direction, wherein the curve in the second direction corresponds to the ridge;

wherein the method is performed by a computer.

6. The computer-implemented method of claim 5, further comprising:

smoothing the height map.

7. The computer-implemented method of claim 5, wherein the first direction is generally perpendicular to the second direction.

8. A computer-implemented method for automatic detection of a groove for an occlusal surface of a patient's tooth, comprising:

a) receiving three dimensional data for the tooth's occlusal surface;

b) projecting the three dimensional data into a two dimensional plane;

c) forming a height map from the projected three dimensional data;

d) forming a set of cubic curves in a first direction from the height map;

e) detecting a low point from the height map data for each of a plurality of cubic curves of the set of cubic curves; and f) linking the low points from the plurality of cubic curves of the set of cubic curves to form a curve in a second direction, wherein the curve in the second direction corresponds to the groove;

wherein the method is performed by a computer.

9. The computer-implemented method of claim 8, further comprising:

smoothing the height map.

10. The computer-implemented method of claim 8, wherein the first direction is generally perpendicular to the second direction.

11. A computer-implemented method for automatic detection of dental features for an occlusal surface of a patient's tooth, comprising:

a) receiving three dimensional data for the tooth's occlusal surface b) projecting the three dimensional data into a two dimensional plane;

c) forming a height map from the projected three dimensional data;

d) forming a set of cubic curves in a first direction from the height map;

e) detecting at least one of a high point and a low point from the height map data for each of a plurality of cubic curves of the set of cubic curves; and f) linking at least one of the high points and the low points from the plurality of cubic curves of the set of cubic curves to form a curve in a second direction;

wherein the method is performed by a computer.

12. The computer-implemented method of claim 11, further comprising detecting local maximum points from the height map to facilitate detection of a plurality of cusps.

13. The computer-implemented method of claim 11, wherein the curve in the second direction corresponds to a ridge.

14. The computer-implemented method of claim 11, wherein the curve in the second direction corresponds to a groove.

15. The computer-implemented method of claim 11, wherein the first direction is generally perpendicular to the second direction.

16. A computerized system for automatic detection of dental features for an occlusal surface of a patient's tooth, said computerized modeling system comprising:

a microprocessor comprising a plurality of algorithms;

a memory device; and wherein said computerized modeling system is configured for:

a) receiving three dimensional data for the tooth's occlusal surface;

b) projecting the three dimensional data into a two dimensional plane;

c) forming a height map from the projected three dimensional data;

d) forming a set of cubic curves in a first direction from the height map;

e) detecting at least one of a high point and a low point from the height map data for each of a plurality of cubic curves of the set of cubic curves; and f) linking at least one of the high points and the low points from the plurality of cubic curves of the set of cubic curves to form a curve in a second direction.

17. The computerized system of claim 16, wherein said computerized modeling system is further configured for detecting local maximum points from the height map.

18. The computerized system of claim 16, wherein the curve in the second direction corresponds to a ridge.

19. The computerized system of claim 16, wherein the curve in the second direction corresponds to a groove.

20. The computerized system of claim 16, wherein the first direction is generally perpendicular to the second direction.

* * * * *